United States Patent [19]

Horber

[11] Patent Number: 4,888,020

[45] Date of Patent: Dec. 19, 1989

[54] FEMUR FOR A KNEE JOINT PROSTHESIS

[75] Inventor: Willi Horber, Zurich, Switzerland

[73] Assignee: Sulzer Brothers Limited, Winterthur, Switzerland

[21] Appl. No.: 587,950

[22] Filed: Mar. 9, 1984

[30] Foreign Application Priority Data

Mar. 23, 1983 [CH] Switzerland .......................... 1595/83

[51] Int. Cl.$^4$ ............................................... A61F 2/38
[52] U.S. Cl. ..................................................... 623/20
[58] Field of Search ......................... 3/1.9, 1.91, 1.911;
128/92 C

[56] References Cited

U.S. PATENT DOCUMENTS 3,798,679  3/1974  Ewald .................................. 3/1.911
4,353,135 11/1982  Forte .................................... 3/1.911

Primary Examiner—Richard J. Apley
Assistant Examiner—David J. Isabella
Attorney, Agent, or Firm—Kenyon & Kenyon

[57] ABSTRACT

The femur part is made for clamping to the end of a femur bone in the manner of a "clamp strap". The femur part includes a backwall having a convex outer surface facing a patella shield which is likewise provided with a facing convex surface. The vertex lines of the respective surfaces define a wedge angle which permits the femur part to be clamped to the femur bone. In addition, the vertex lines of the two surfaces are located in a common connecting plane which is perpendicular to the respective tangential planes passing through the vertex lines. The wedge angle may extend up to 30°.

9 Claims, 4 Drawing Sheets

FEMUR FOR A KNEE JOINT PROSTHESIS

This invention relates to a femur part for a knee joint prosthesis.

As is known, various types of femur parts have been provided for knee joint prostheses. For example, in some cases, the femur part has been constructed with a pair of condyle shells which are connected together frontally by a patella shield which, in turn, merges by way of a femoral plateau into a backwall which dorsally connects the condyle shells. Generally, this type of femur part is intended for a so-called partial prosthesis which is usually intended for use where at least functional lateral ligaments are required. Such prostheses, for example as described in German No. OS 22 21 913, are frequently not provided with an actual anchoring shank in the femur part for extending into a medullar cavity of a femur. Instead, at most, the femoral plateau has usually been provided with pins which can be inserted into the "bulges" of the condyles possibly with the aid of a bone cement.

Accordingly, it is an object of the invention to provide a femur part for a knee joint prosthesis which can be anchored to a femur in a primary retention manner at least until accreting and ingrowing tissue fixes the part to the femur.

It is another object of the invention to provide a femur part for a knee joint prosthesis which can be held in place on a femur without the need for bone cement.

It is another object of the invention to provide a femur part for a knee joint prosthesis which can be held on a femur without need of an anchoring shank.

Briefly, the invention provides a femur part for a knee joint prosthesis which comprises a pair of condyle shells, a platella shield which connects the shells together frontally and a backwall which connects the shells together dorsally In addition, the patella shield has a rearwardly facing convex surface while the backwall has a convex outer surface of these surfaces has a vertex line which is disposed in a common connecting plane. Further, the vertex lines are mutually juxtaposed nearest each other to define an wedge angle therebetween which converges distally of from greater than 0° to 30°. Also, the common connecting plane is perpendicular to a respective tangential plane which passes through each of the vertex lines.

By directing the convex surfaces of the patella shield and the backwall towards each other, a "clamp strap" is formed so that during an operation, the femur part can be slipped onto a femur bone which has been prepared with the utmost protection of the bone substance. The clamping union which is created insures a cement-free primary anchoring, or one which requires little cement, of the femur part to the bone. In the course of time, the union is strengthened more and more by ingrowing and accreting bone tissue.

The femur part may also be provided with a femoral plateau which connects the platella shield to the backwall. In addition, pins may be provided on this femoral plateau to penetrate into the condyle bulges of the femur.

Advantageously, the bisector of the wedge angle forms an angle of, at most, one-half of the wedge angle with a surface normal to a tangential plane passing through a vertex of the condyle shells. This insures that the vertex lines of the outer surfaces of the shield and backwall are rotated about an axis parallel to the axis of rotation of the joint so that, at most, one of the vertex lines extends parallel to a plane in which the femur axis lies. This prevents the vertex lines from being "turned too far" so that the vertex lines cannot form an acute angle with the axial plane which opens downwardly. Apart from this restriction, the position of the vertex lines and, hence, the form and position, of both convex surfaces can be selected freely to a large extent In particular, the common connecting plane of the two vertex lines may be either parallel to the sagittal plane or inclined relative to the sagittal plane in the medial or lateral direction and/or may be rotated about the surface normal of the tangential plane passing through the vertex of the condyle shells.

The patella shield is also constructed in asymmetric relation relative to the sagittal plane between the condyle shells in order to take into account, at least approximately, the asymmetry of natural left and right knee joints.

The femur part may be made of any suitable materials and/or material combinations used in implant technology provided the materials have the necessary elastic pliancy. Preferred materials include metals and metal alloys, particularly cobalt or titanium alloys, fiber-reinforced plastics as well as carbon and carbide compounds.

These and other objects and advantages of the invention will become more apparent from the following detailed description taken in conjunction with the accompanying drawings wherein.

Figure 1:
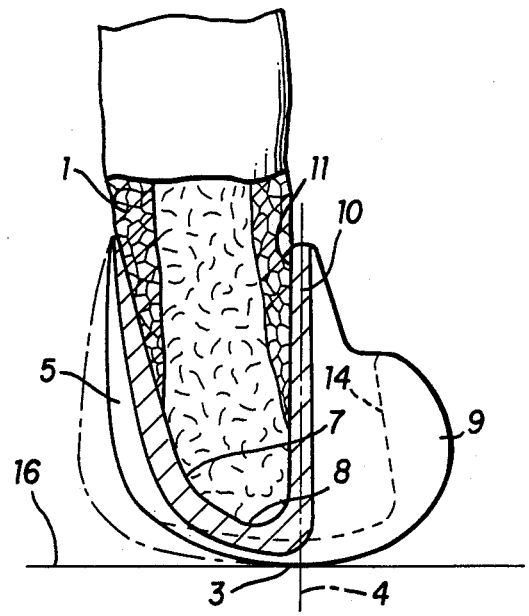
FIG. 1 illustrates a view taken on line I—I of FIG. 2 of a femur part clamped to a femur bone.
Figure 4:
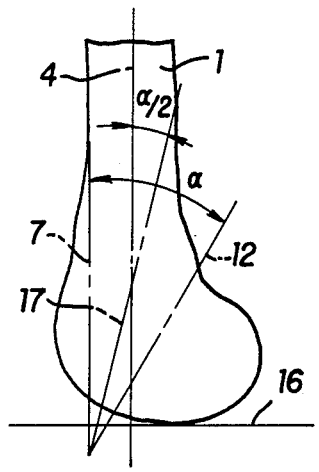
Figure 5:
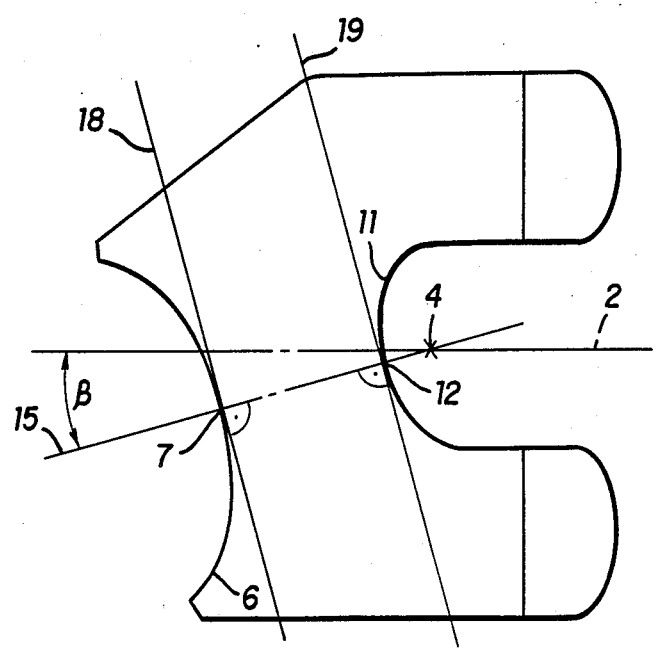
Figure 6:
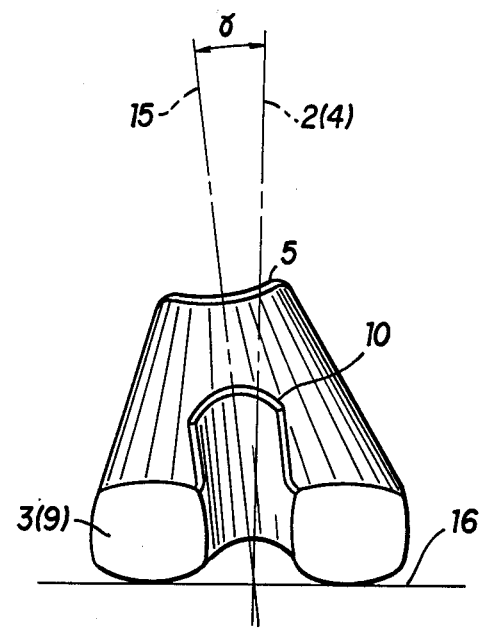
Figure 7:
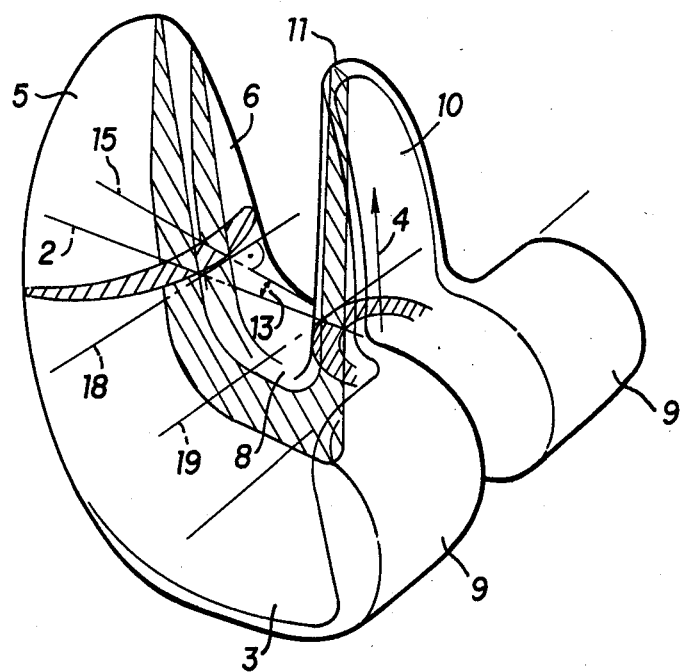

FIG. 4 schematically represents the limit positions of the vertex lines of the femur part of FIG. 1;

FIG. 5 illustrates a plan view of a femur part wherein the common connecting plane of the vertex lines is rotated relative to the sagittal plane in accordance with the invention;

FIG. 6 illustrates a view in the dorsal/ventral direction of a femur part wherein the common connecting plane of the vertex lines is inclined on the sagittal plane in a medial/lateral direction; and FIG. 7 illustrates a perspective view of the femur part of FIG. 1.

Figure 2:
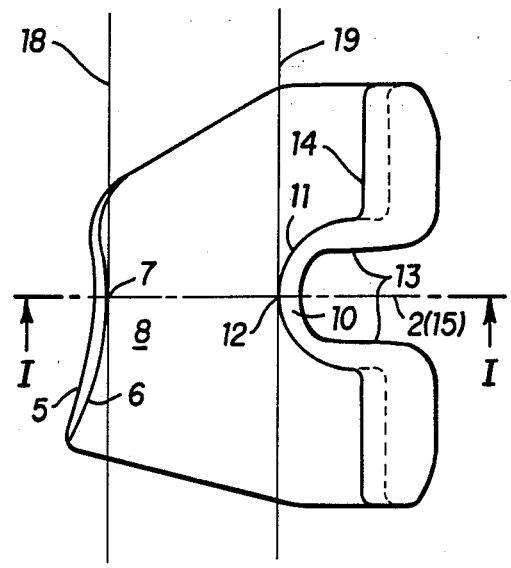
FIG. 2 illustrates a plan view of the femur part of FIG. 1.

Referring to FIGS. 1 and 2, the femur part which is to be fixed at the distal end of a femur bone 1 (FIG. 1) is provided with a pair of condyle shells 3. As indicated in FIG. 2, each shell 3 is of condyloid form on the exterior and is located to one side of a sagittal plane 2. During movement of the knee joint, the shells 3 roll off in a sliding manner on a tibia part (not shown) and in so doing essentially transmit the load forces through the knee joint. As indicated, in FIG. 1, when the knee joint is in a straightened position, a tangential plane 16 to the vertex of the condyle shells 3 is substantially horizontal. In addition, a surface normal 4 to the tangential plane 16 at the vertex of the condyle shells 3 is vertical.

Figure 3:
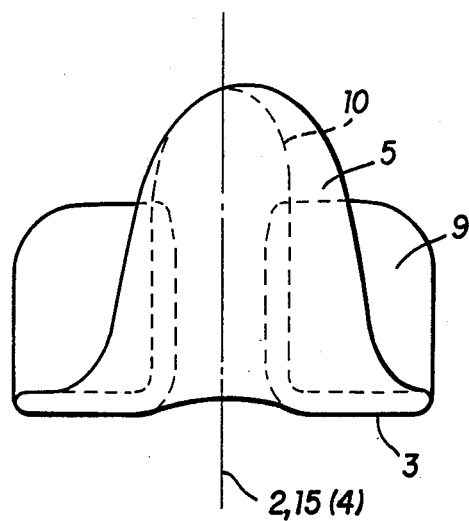
FIG. 3 illustrates a frontal view of the femur part of FIG. 1.

The femur part also has a patella shield 5 which connects the condyle shells together frontally. This shield 5 has a rearwardly facing convex surface 6 which, in this example, represents a segment from the outer surface of a hollow cylinder. In relation to the sagittal plane 2, the patella shield 5 has an asymmetrical form so that the area of the patella shield is greater in the lateral direction, i.e. toward the outside rather than edially (see FIG. 3). As such, the femur part illustrated is intended for a left femur bone 1.

The femur part also has a femoral plateau 8 which connects the patella shield 5 to a backwall 10. This backwall 10 connects the dorsal regions 9 of the condyle shells together and has a convex outer surface 11 facing the patella shield 5, which, in this example consists of a segment of a hollow cylinder. As indicated in FIG. 1, the backwall 10 stands upright in the direction of the surface normal 4. As shown in FIG. 2, the convex surfaces 6, 11 face each other and are adapted to engage opposite sides of the femur bone 1 as shown in FIG. 1. In addition, the mutually nearest juxtaposed generatrices of the two convex surfaces 6, 11 form vertex lines 7, 12 which extend so as to lie in a common connecting plane 15 and not in separate intersecting planes. As indicated in FIG. 1, the vertex lines 7, 12 define an acute wedge angle which converges distally of 15°. In addition, the connecting plane 15 is perpendicular to the two tangential planes 18, 19 passing through the vertex lines 7, 12 and coincides with the sagittal plane 2.

Referring to FIG. 2, the approximately semi-cylindrical shell of the backwall 10 changes over into a pair of straight vertical sidewalls 13 which merge into the dorsal regions 9 of the condyle shell 3. As indicated in FIG. 1, the sidewalls 13 extend away from the femur bone 1.

The hollow cylinder creating the patella shield 6 has a considerably greater radius of curvature than the low cylinder of the backwall 10 in this example. The hollow cylinder of the backwall 10 in this example, The radii of curvature are selected so as to facilitate adaptation of the convex outer surfaces 6, 11 to the form of the femur bone 1 in the respective regions.

To insure a clamping strap effect, the vertex lines 7, 12 form a wedge angle which may be of a value of up to 30°. For example the wedge angle α may be in the range of from greater than 0° to 30°. As indicated in FIG. 1, the vertex line 12 is in one limit condition in that the vertex line 12 extends parallel to the surface normal 4 whereas the vertex line 7 is inclined. In the other limit condition as indicated in FIG. 4, the vertex line 7 is parallel to the surface normal 4 while the dorsal vertex line 12 is inclined. Of course, it is also possible to have both vertex lines 7, 12 inclined to the surface normal 4. As further indicated in FIG. 4, the bisector of the wedge angle α forms an angle of α/2 with the surface normal 4.

As indicated in FIG. 1, the dorsal regions 9 of the condyle shells 3 have inner surfaces 14 which may abut on the femur bone 1 and which are slightly inclined relative to the surface normal 4. The purpose of this inclination is to make unintentional "slipping off" of the femur part from the bone 1 difficult and to make it possible that the condyle shells 3 can be brought forward again relatively far at the top with minimum bone resection. Thus, a large roll-off region at extreme bending of the knee joint is created.

As mentioned above and as especially shown in FIG. 3, the patella shield 5 is given an as asymmetric form relative to the sagittal plane 2 although the vertex line 7 extends in the sagittal plane 2. The larger surface area share of the patella shield is thus situated laterally of the sagittal plane 2. This asymmetry has the advantage of achieving an improved approximation as compared to a symmetrical shield, to the physiological facts concerning the patella "sliding" on the shield 5.

With respect to the form of the convex surfaces 6, 11, this form is not limited to bodies with circular-cylindrical cross-sections. Instead, elliptical, oval or other cross-sectional forms such as polygonal are also possible. Further, the radii of these cross-sectional shapes may increase in the distal direction so that the generatrices diverge conically as indicated in FIG. 6. However, the vertex lines 7, 12 with the shortest distance a (see FIGS. 2 and 5)always define a common connecting plane 15 which, in the embodiment illustrated in FIGS. 1 to 3, coincides with the sagittal plane 2.

Referring to FIGS. 5 and 7, the common connecting plane 15 and, hence, the vertex lines 7, 12 which primarily bring about the described clamping effect may extend obliquely to the sagittal plane 2. That is, the common connecting plane 15 may be inclined in a lateral or medial direction and/or may be rotated relative to the sagittal plane 2 about the surface normal 4 as an axis of rotation. As indicated, the angle of rotation 8 from the sagittal plane 2 toward each side can amount to from 0° to 20°.

Referring to FIG. 6, the connecting plane 15 of the vertex lines 7, 12 may be inclined to the sagittal plane 2 as shown. In this case, the angle of inclination γ may assume values in the medial direction of up to 5° and in the lateral direction of up to 12°. Naturally, other positions of the femur part are possible where the connecting plane 15 is inclined and rotated simultaneously.

The invention thus provides a femur part which can be readily clamped to the lower end of a femur bone and held in place in a cement free primary anchoring manner. During an operation, the femur part can be readily slipped onto a femur bone which has been suitable prepared.

What is claimed is:

1. A femur part for a knee joint prosthesis comprising
a pair of condyle shells;
a patella shield connecting said shells together frontally and having a rearwardly facing convex surface;
a backwall connecting said shells, together dorsal and having a convex outer surface facing said patella shield and
a femoral plateau connecting said patella shield to said backwall;
wherein each said surface has a vertex line disposed in a common connecting plane, said lines being mutually juxtaposed near each other to define an acute wedge angle therebetween converging distally of from greater than 0° to 30°, said plane being perpendicular to a respective tangential plane passing through each said vertex line.

2. A femur part as set forth in claim 1 wherein a bisector of said wedge angle forms an angle of at most one-half said wedge angle with a surface normal to a tangential plane passing through a vertex of said condyle shells.

3. A femur part as set forth in claim 1 wherein said common connecting plane is inclined to a sagittal plane in one of a medial or lateral direction.

4. A femur part as set forth in claim 1 wherein said patella shield is asymmetric relative to a sagittal plane between said condyle shells.

5. A femur part for a knee joint prosthesis comprising
a pair of condyle shells;
a patella shield connecting said shells together ventrally and having a rearwardly facing convex surface;

a backwall connecting said shells together dorsally and having a convex outer surface facing said patella shield to engage a femur bone therebetween; and each said surface having a vertex line disposed in a common connecting plane, said plane being perpendicular to a respective tangential plane passing through each said vertex line.

6. A femur part as set forth in claim 5 wherein said vertex lines define an acute wedge angle therebetween.

7. A femur part as set forth in claim 6 wherein said wedge angle (a) is $0 < \alpha < 30°$.

8. A femur part as set forth in claim 5 wherein said vertex lines are mutually juxtaposed nearest each other.

9. A femur part as set forth in claim 5 wherein said common connecting plane is inclined to a sagittal plane in one of a medial or lateral direction.

* * * * *

UNITED STATES PATENT AND TRADEMARK OFFICE
CERTIFICATE OF CORRECTION

PATENT NO. : 4,888,020
DATED : December 19, 1989
INVENTOR(S) : WILLI HORBER

It is certified that error appears in the above-identified patent and that said Letters Patent is hereby corrected as shown below:

Column 1, line 40 "surface of" should be -surface facing the patella. In accordance with the invention, each of --
Column 3, line 29 "low" should be -hollow-
Column 3, lines 30, 31 "The ... example," should be deleted
Column 3, line 61 "as" should be deleted
Column 4, line 19 "8" should be -B-

Column 4, line 41 "dorsal" should be -dorsally-
Column 4, line 41, "shells, together dorsal" should read -- shells together dorsally--.

Signed and Sealed this

Twelfth Day of February, 1991

Attest:

HARRY F. MANBECK, JR.

*Attesting Officer*          *Commissioner of Patents and Trademarks*